US012582413B2

(12) United States Patent
Stump et al.

(10) Patent No.: US 12,582,413 B2
(45) Date of Patent: Mar. 24, 2026

(54) SURGICAL INSTRUMENT

(71) Applicant: BAK Kohler Medical KG, Neuhausen ob Eck (DE)

(72) Inventors: Klaus Stump, Neuhausen ob Eck (DE); Andreas Kohler, Eigeltingen/Honstetten (DE)

(73) Assignee: BAK KOHLER MEDICAL KG, Neuhausen ob Eck (DE)

( * ) Notice: Subject to any disclaimer, the term of this patent is extended or adjusted under 35 U.S.C. 154(b) by 62 days.

(21) Appl. No.: 18/368,912

(22) Filed: Sep. 15, 2023

(65) Prior Publication Data

US 2024/0268837 A1     Aug. 15, 2024

(30) Foreign Application Priority Data

Feb. 14, 2023    (DE) ..................... 10 2023 103 519.3

(51) Int. Cl.
A61B 17/16          (2006.01)

(52) U.S. Cl.
CPC ................................ A61B 17/1611 (2013.01)

(58) Field of Classification Search
CPC ............ A61B 17/1608; A61B 17/1611; A61B 17/1606
See application file for complete search history.

(56) References Cited

U.S. PATENT DOCUMENTS

| | | | |
|---|---|---|---|
| 5,961,531 A | 10/1999 | Weber et al. | |
| 8,048,106 B2 | 11/2011 | Widmann | |
| 8,206,408 B2 | 6/2012 | Rebstock et al. | |
| 2010/0222800 A1* | 9/2010 | Rebstock | A61B 17/1611 |
| | | | 606/184 |
| 2015/0201950 A1* | 7/2015 | Fetzer | A61B 17/1604 |
| | | | 606/83 |
| 2017/0086858 A1* | 3/2017 | Schreider | A61B 17/1611 |

FOREIGN PATENT DOCUMENTS

| | | |
|---|---|---|
| DE | 19921614 B4 | 9/2004 |
| DE | 102010006846 A1 | 9/2010 |
| DE | 102006012754 B4 | 7/2020 |
| EP | 2213254 A1 | 8/2010 |
| WO | 2021259066 A1 | 12/2021 |

OTHER PUBLICATIONS

European Search Report dated Jun. 19, 2024, of European counterpart application No. EP 24157261.9 and English Language Translation thereof.
Office Action issued in German Patent Application No. DE 10 2023 103 519.3, dated Jan. 10, 2024, (from which this application claims priority) and English machine translation thereof.

* cited by examiner

*Primary Examiner* — Samuel S Hanna
(74) *Attorney, Agent, or Firm* — Ewers IP Law PLLC; Falk Ewers

(57)          ABSTRACT

The present disclosure relates to a surgical instrument for punching bones, including a shaft having a first cutting element, a sliding part having a second cutting element slidably arranged on the shaft in a working position, and a folding device for beak-like unfolding of the sliding part and the shaft in a cleaning position, including a spreading device for spreading the sliding part and the shaft.

13 Claims, 3 Drawing Sheets

SURGICAL INSTRUMENT

CROSS REFERENCE TO RELATED APPLICATIONS

This application claims priority to German patent application DE 10 2023 103 519.3, filed Feb. 14, 2023, the entire content of which is incorporated herein by reference.

TECHNICAL FIELD

The present disclosure relates to a surgical instrument for punching bones.

BACKGROUND

EP 2 213 254 B1 relates to a surgical instrument including a shaft and a sliding part which is longitudinally displaceable relative to the shaft. Instruments of this type are unwieldy during cleaning.

SUMMARY

It is an object of the present disclosure to provide a surgical instrument that can be cleaned in a simpler manner.

The object is achieved by a surgical instrument for punching bones as described herein.

According to a first aspect of the disclosure, the object is solved by a surgical instrument for punching bones which includes a shaft having a first cutting element, a sliding part having a second cutting element slidably arranged on the shaft in a working position, and a folding device for beak-like unfolding of the sliding part and the shaft in a cleaning position, which includes a spreading device for spreading the sliding part and the shaft. In the cleaning position, the sliding part is secured such that it cannot be accidentally locked when the slider is folded up.

In an exemplary embodiment of the surgical instrument, the spreading device includes a spreading spring. This provides the technical advantage, for example, that the spreading device can be realized with little effort.

In another exemplary embodiment of the surgical instrument, the spreading device is arranged between the shaft and the sliding part. This provides the technical advantage, for example, that a compact design is achieved.

In another exemplary embodiment of the surgical instrument, the spreading device is configured to press the sliding part against a stop element. This provides the technical advantage, for example, that the maximum opening angle is limited in the cleaning position.

In another exemplary embodiment of the surgical instrument, the stop element is positioned fixedly. This provides the technical advantage, for example, that the maximum opening angle in the cleaning position is unchangeable.

In another exemplary embodiment of the surgical instrument, the stop element is formed by a screw. This provides the technical advantage, for example, that the stop element can be formed in a simple manner.

In another exemplary embodiment of the surgical instrument, the spreading device is arranged around the screw. This also provides the technical advantage, for example, that a compact design is achieved.

In another exemplary embodiment of the surgical instrument, the maximum spread angle in the cleaning position is 5°. This provides the technical advantage, for example, of ensuring good operability of the surgical instrument in the cleaning position.

In another exemplary embodiment of the surgical instrument, the sliding part cannot be displaced relative to the shaft in the cleaning position. This provides the technical advantage, for example, that unintentional closing of the surgical instrument during cleaning can be prevented.

In another exemplary embodiment of the surgical instrument, the shaft has a guide profile for guiding the sliding part. This provides the technical advantage, for example, that the sliding part is guided on the shaft so that it cannot be lost.

In another exemplary embodiment of the surgical instrument, the guide profile ends in a recess in which the sliding part is released. This provides the technical advantage, for example, that this can be moved into the cleaning position with an unfolding movement by the spreading element.

In another exemplary embodiment of the surgical instrument, the surgical instrument includes a push button which forms a stop for a handle element in the working position. This provides the technical advantage, for example, of limiting the movement of the sliding part.

In another exemplary embodiment of the surgical instrument, the stop is released when the push button is actuated. This provides the technical advantage, for example, that the sliding part can reach the cleaning position.

In another exemplary embodiment of the surgical instrument, the push button is arranged in the actuation handle. This provides the technical advantage, for example, that the push button can be actuated in a simple manner.

In another exemplary embodiment of the surgical instrument, the surgical instrument is a laminectomy rongeur. This provides the technical advantage, for example, of using particularly suitable surgical tools.

BRIEF DESCRIPTION OF THE DRAWINGS

The disclosure will now be described with reference to the drawings wherein.

DESCRIPTION OF EXEMPLARY EMBODIMENTS

Figure 1:
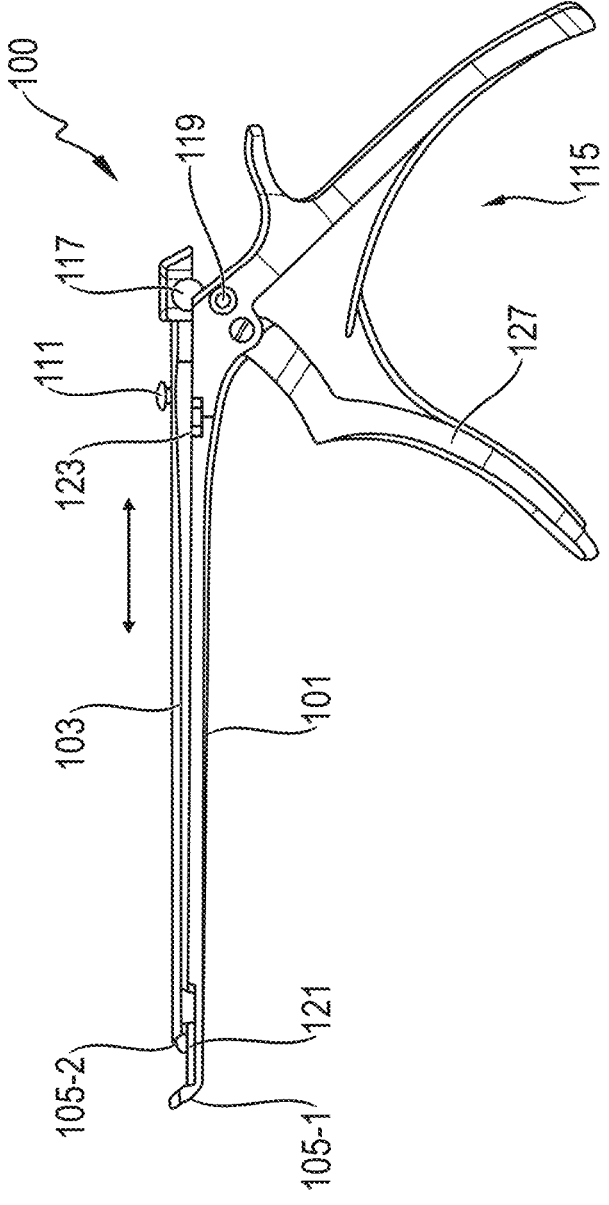
FIG. 1 shows an illustration of a surgical instrument in a working position.

FIG. 1 is an illustration of a surgical instrument 100 in a working position. The surgical instrument 100 is, for example, a laminectomy rongeur and is used to remove bone tissue at locations that are difficult to access. For this purpose, the surgical instrument 100 includes an elongated shaft 101 having a first cutting element 105-1 and a sliding part 103 having a second cutting element 105-2. The sliding part 103 is longitudinally slidably guided on the shaft 101.

The surgical instrument 100 includes an actuation handle 115 with a rotatably mounted handle element 127. In a working position of the surgical instrument 100, when the actuation handle 115 is actuated, the sliding part 103 is pushed forward such that the two cutting elements 105-1 and 105-2 move towards each other and then close. This makes it possible to remove bone tissue lying between the two cutting elements 105-1 and 105-2. If the actuation handle 115 is released, the sliding part 103 moves in the opposite direction until the movement of the actuation handle 115 is limited by a push button 119.

The sliding movement is transmitted by a cylindrical head 117 from the rotatably mounted actuation handle 115 to the sliding part 103. For this purpose, the sliding part 103 is guided on the shaft 101 slidably via a groove-like guide profile 121. The guide profile 121 ends in a recessed end region 123. In the working position of the surgical instrument 100, a slot nut of the sliding part 103 cannot reach the recessed end regions 123, so that detachment of the sliding part 103 from the shaft 101 is precluded.

After a use of the surgical instrument 100, it is cleaned and sterilized. To do this, the actuation handle 115 is pushed lightly to take a tension from a push button 119 for release to the cleaning position. Actuating the push button 119 and further depressing the actuation handle 115 moves the sliding part 103 back to a position outside the guide profile 121 on the shaft 101, at which the slot nut moves into the recessed end regions 123. The guiding of the sliding part 103 on the shaft is thereby disengaged.

Manual actuation of the push button 119 and simultaneous depressing of the biased actuation handle 115 unlocks the surgical instrument 100, thereby achieving a cleaning position. Initial pressing of the biased actuation handle 115 relieves the pressure on the push button 119 such that it can also be pressed and actuated manually. Further actuation of the actuation handle 115 while the push button 119 is depressed moves the sliding part 103 subsequently into the cleaning position. This mechanism can be used to ensure that the surgical instrument 100 cannot unintentionally move from the working position to the cleaning position.

Figure 2:
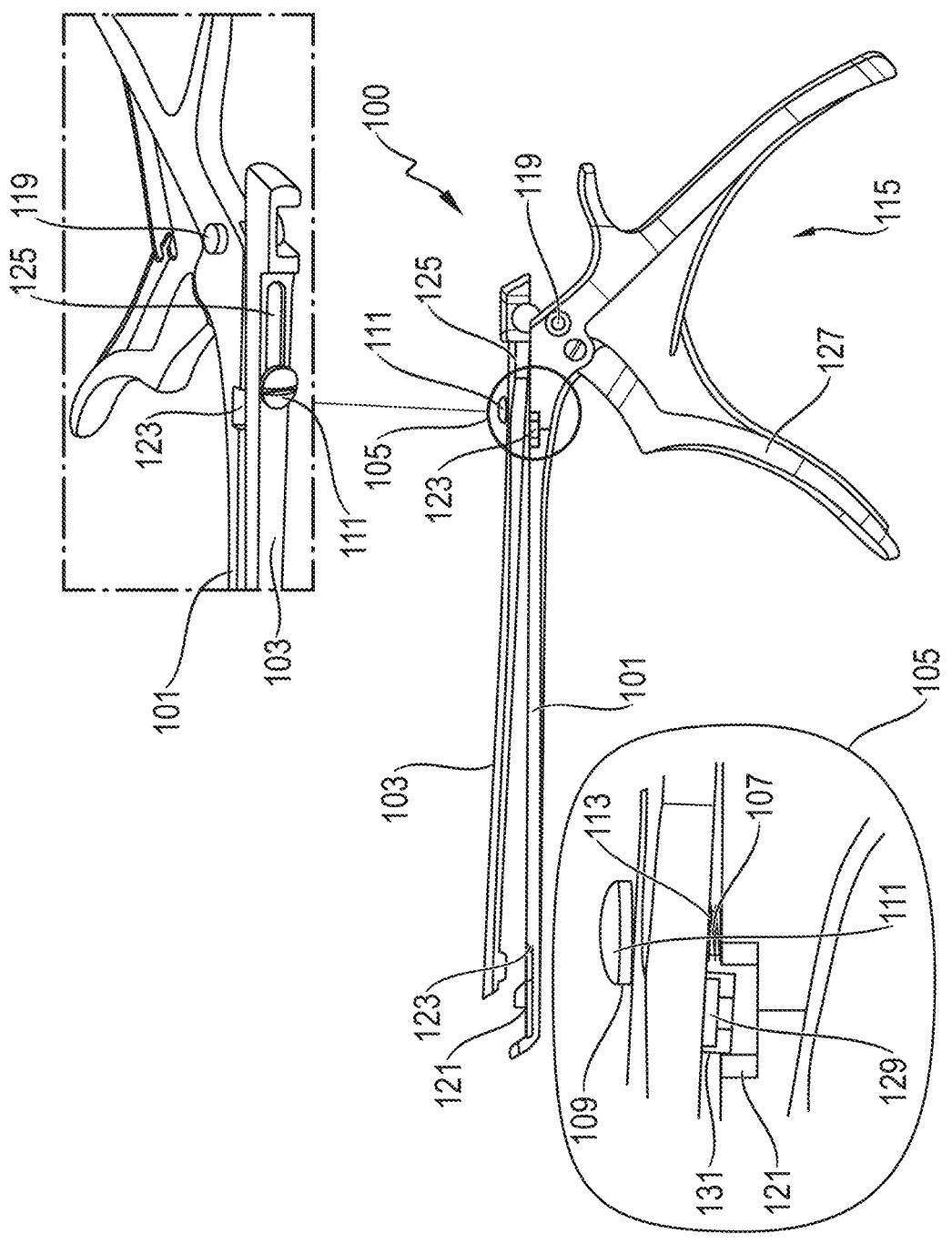
FIG. 2 shows an illustration of the surgical instrument in a cleaning position.

FIG. 2 shows an illustration of the surgical instrument 100 in the cleaning position. Due to the released guide in the cleaning position, the sliding part 103 opens upwards in a beak-like manner and unfolds. Through the unfolded shaft 101 and the sliding part 103, it is then possible to clean the surgical instrument 100 in the region between the two elements.

Unfolding is achieved by a folding device 105, which includes a spreading device 107 for automatically spreading the sliding part 103 and the shaft 101. The spreading device can be formed, for example, by an integrated spreading spring 113, which automatically pushes the shaft 101 and the sliding part 103 apart in the cleaning position.

The spreading spring 113 presses the sliding part 103 against a stop element 109 formed by a screw 111 having a screw head. The screw 111 is attached to the shaft and is located in an elongated recess 125 within the sliding part 103. The screw 111 is attached such that rotation is prevented and such that it forms a fixedly positioned stop element 109 and the maximum opening angle cannot be changed in the cleaning position.

As a result, the sliding part 103 remains movable along the shaft 101. The recess 125 is larger than the diameter of the screw 111, such that the sliding part 103 can also move laterally in the cleaning position due to the play of the screw 111 in the recess 125.

With the stop element 109, the unfolding angle between the shaft 101 and the sliding part 103 is limited. The spreading spring 113 is arranged between the shaft 101 and the sliding part 103 and around the screw 111. This provides the advantage that the spreading spring 113 is fixed by the screw 111.

In the cleaning position, the sliding part 103 cannot be lost or interchanged. In the open cleaning position, the sliding part 103 cannot be moved forward even when the handle element 127 is actuated, but is locked in the rear position. Lateral rotation of the sliding part 103 with respect to the shaft 101 is also blocked, such that this can only be folded shut in the direction of the shaft 101.

Only after a compression of the sliding part 103 and the shaft 101, the sliding part 103 can be moved along the shaft again when the handle element 127 is actuated.

This is achieved in that a T-shaped slot nut 129, which is arranged on the sliding part 103, is located above the guide profile 121 of the shaft 101 in the cleaning position and abuts against an edge 131 when the handle element 127 is actuated. This blocks a displacement of the sliding part 103. This is achieved by the fixed and unchangeable opening angle in the cleaning position and the spreading device 107. Only after the sliding part 103 and the shaft 101 have been pressed together can the slot nut 129 be picked up again by the internal guide 121 such that the sliding part 103 can be moved forward.

The surgical instrument 100 is easily disassembled and easy to handle and easier to assemble after cleaning.

Figure 3:
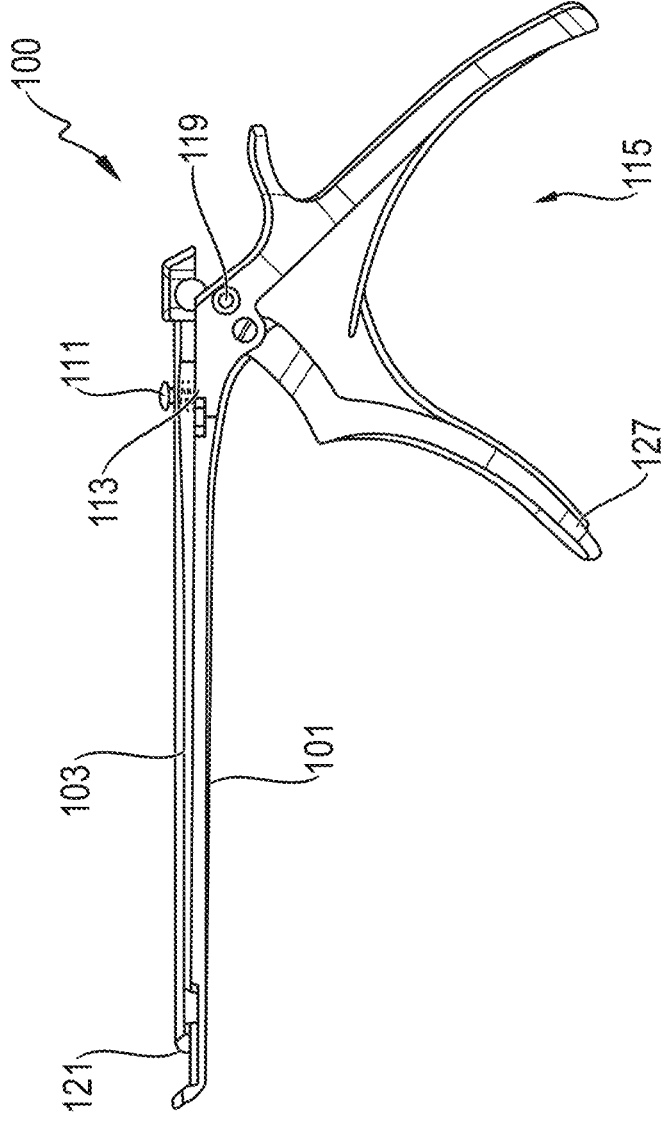
FIG. 3 shows an illustration of the surgical instrument in the working position.

FIG. 3 shows another illustration of the surgical instrument 100 in the working position. To reach the working position, the sliding part 103 is manually pushed downwards so that it comes to rest again on the shaft 101. By slightly actuating the actuation handle 115, the sliding part 103 moves in the direction of the guide profile 121 such that the guidance of the sliding part is restored. The sliding part 103 again engages in the working position. In this way, the technical advantage is achieved that the cleaning position is secured, in which the sliding part 103 cannot be locked accidentally when it is folded upwards.

All of the features explained and shown in connection with exemplary embodiments of the disclosure may be provided in different combinations in the subject matter of the disclosure to simultaneously realize their beneficial effects.

It is understood that the foregoing description is that of the exemplary embodiments of the invention and that various changes and modifications may be made thereto without departing from the spirit and scope of the invention as defined in the appended claims.

LIST OF REFERENCE NUMERALS

100 surgical instrument
101 shaft
103 sliding part
105 folding device
107 spreading device
109 stop element
111 screw
113 spreading spring
115 actuation handle
117 button
119 push button
121 guide profile
123 end region
125 recess
127 handle element
129 slot nut

What is claimed is:

1. A surgical instrument for punching bones, comprising:
a shaft having a first cutting element;
a sliding part having a second cutting element, which is slidably arranged on the shaft in a working position of the sliding part;
an actuation handle including a handle element arranged rotatably relative to the shaft, wherein when the actuation handle is actuated in the working position of the sliding part, the sliding part slides relative to the shaft in a sliding direction;

a push button which, when actuated together with the actuation handle, allows the sliding part to be moved to a cleaning position; and a folding device for beak-like unfolding of the sliding part and the shaft in the cleaning position of the sliding part, wherein the folding device comprises a spreading spring arranged perpendicular to the longitudinal direction of the shaft between the sliding part and the shaft and configured to move the sliding part relative to the shaft in a direction traverse to the sliding direction when the sliding part is in the cleaning position.

2. The surgical instrument according to claim 1, wherein the spreading spring is configured to press the sliding part against a stop element.

3. The surgical instrument according to claim 2, wherein the stop element is fixedly positioned.

4. The surgical instrument according to claim 2, wherein the stop element is formed by a screw.

5. The surgical instrument according to claim 4, wherein the spreading spring is arranged around the screw.

6. The surgical instrument according to claim 1, wherein a maximum spread angle in the cleaning position is 5°.

7. The surgical instrument according to claim 1, wherein, in the cleaning position, the sliding part cannot be displaced relative to the shaft in the longitudinal direction of the shaft.

8. The surgical instrument according to claim 1, wherein the shaft has a guide profile for guiding the sliding part.

9. The surgical instrument according to claim 8, wherein the guide profile terminates in a recess in which the sliding part is released.

10. The surgical instrument according to claim 1, wherein the push button forms a stop for the handle element in the working position.

11. The surgical instrument according to claim 10, wherein upon actuation of the push button the stop is released.

12. The surgical instrument according to claim 1, wherein the push button is arranged in the actuation handle.

13. The surgical instrument according to claim 1, wherein the surgical instrument is a laminectomy rongeur.

* * * * *